United States Patent [19]
deVilliers

[11] Patent Number: 4,963,481
[45] Date of Patent: Oct. 16, 1990

[54] PROMOTER SYSTEM
[75] Inventor: Jean P. deVilliers, Boston, Mass.
[73] Assignee: Genetics Institute Inc, Cambridge, Mass.
[21] Appl. No.: 929,969
[22] Filed: Nov. 12, 1986

Related U.S. Application Data

[63] Continuation-in-part of Ser. No. 810,819, Dec. 18, 1985.
[51] Int. Cl.[5] .................. C12P 21/00; C12N 15/00; C12N 15/11; C12N 15/86
[52] U.S. Cl. .................. 435/69.1; 435/70.1; 435/172.3; 435/235; 536/27; 935/60; 935/70; 935/32; 935/36
[58] Field of Search ............ 435/68, 90, 91, 235, 435/253, 132.3, 317; 536/27; 935/32, 34, 36, 41, 56, 57, 71

[56] References Cited

PUBLICATIONS de Villiers et al. (1982) *Nucleic Acids Research*, vol. 10, pp. 7965-7974.
Pasleau et al. (1985), *Gene*, vol. 38, pp. 227-232.
Jeang et al. (1984), *Molecular and Cellular Biology*, vol. 4, pp. 2214-2223.
Thomsen et al. (1984), *Proceedings of the National Academy of Sciences*, U.S.A., vol. 81, pp. 659-663.
Boshart et al. (1985), *Cell*, vol. 41, pp. 521-530.
Sassone-Corsi et al. (1981), *Nucleic Acids Research*, vol. 9, pp. 3941-3958.
Jove et al. (1984), *J. Biological Chemistry*, vol. 259, pp. 8513-8521.
Dorsch-Hasler et al., 1986, Proc. Natl. Acad. Sci., U.S.A. 82:8325-8329.
de Villiers et al., 1981, Nucleic Acids Res. 9:6251-6264.
de Villiers et al., 1982, Cold Spring Harbor Symp. Quant. Biol. XVLII, Cold Spring Harbor Laboratory, pp. 911-919.
de Villiers et al., 1983, Techniques in Nucleic Acid Biochemistry, vol. B507 (ed. R. Flavell), Elsevier, pp. 2-20.
de Villiers et al., 1983, Enhancers and Eukaryotic Gene Expression (eds. Gluzman & Shenk), Cold Spring Harbor Laboratory, pp. 55-61.
Weber et al., 1984, Adv. Gene Technol. 1:48-51.
Weber et al., 1984, Cell 36:983-992.
de Villiers et al., 1984, Nature, 312:242-246.
Jasin et al., 1985, Cell 42:695-703.
Cowie et al., 1986, Mol. Cell. Biol. 6:4344-4352.
de Villiers, 1985, S.A. Journal of Science 82:479-482.
de Villiers et al., 1981, Experientia 37:642.
Banerji, de Villiers,Rusconi & Schaffner, 1981, Imperial Cancer Research Fund DNA Tumour Virus Meeting Abstract Booklet.
de Villiers et al., 1982, Experientia 38:739.
de Villiers, Tyndall, Olson, Kamen & Schaffner, 1982, Cold Spring Harbor DNA Tumour Virus Meeting Abstract Booklet.
Gerster et al., 1983, Experientia 39:401.
de Villiers, Lupton, Tyndall, Schaffner & Kamen, 1984, Abstract booklet of the 5th German-Soviet Symposium.
de Villiers, Schaffner, Tyndall, Lupton & Kamen, 1984, Cold Spring Harbor DNA Tumour Virus Meeting Abstract Booklet.
de Villiers, 1985, Functional Analysis of Transcriptional Enhancers, Inaugural-Disseratation zur Erlangung der philosophischen Doktorwurde vorgelegt der Philosophischen Fakultat II der Universitat Zurich—Begutachtet von Herrn Prof. Dr. W. Schaffner.
Banerji et al., 1982, Experientia 38:736.
Stenberg et al., 1984, J. Virology 49:190-199.
Jahn et al., 1984, J. Virology 49:363-370.
Veldman et al., 1985, Mol. Cell. Biol. 5(4):649-658.

Primary Examiner—Richard A. Schwartz
Assistant Examiner—Stephanie Seidman
Attorney, Agent, or Firm—David L. Berstein; Bruce M. Eisen

[57] ABSTRACT

Recombinant DNA molecules are disclosed which contain a nucleotide sequence encoding a mouse cytomegalovirus-derived transcriptional promoter. Eucaryotic host cells transformed with recombinant DNA molecules having such mouse cytomegalovirus-derived promoter sequences operatively linked to heterologous protein-coding sequences may be cultured as a method for producing the heterologous proteins or as a method for identifying and isolating DNA encoding the heterologous protein via any method involving detection of the protein.

5 Claims, 9 Drawing Sheets

```
           10         20         30         40         50
      →
      AACTCCGCCC GTTTTATGAC TAGAACCAAT AGTTTTTAAT GCCAAATGCA
      TTGAGGCGGG CAAAATACTG ATCTTGGTTA TCAAAAATTA CGGTTTACGT 60         70         80         90        100
      CTGAAATCCC CTAATTTGCA AAGCCAAACG CCCCCTATGT GAGTAATACG
      GACTTTAGGG GATTAAACGT TTCGGTTTGC GGGGGATACA CTCATTATGC 110        120        130        140        150
      GGGACTTTTT ACCCAATTTC CCAAGCGGAA AGCCCCCTAA TACACTCATA
      CCCTGAAAAA TGGGTTAAAG GGTTCGCCTT TCGGGGATT ATGTGAGTAT 160        170        180        190        200
      TGGCATATGA ATCAGCACGG TCATGCACTC TAATGGCGGC CCATAGGGAC
      ACCGTATACT TAGTCGTGCC AGTACGTGAG ATTACCGCCG GGTATCCCTG 210        220        230        240        250
      TTTCCACATA GGGGGCGTTC ACCATTTCCC AGCATAGGGG TGGTGACTCA
      AAAGGTGTAT CCCCCGCAAG TGGTAAAGGG TCGTATCCCC ACCACTGAGT 260        270        280        290        300
      ATGGCCTTTA CCCAAGTACA TTGGGTCAAT GGGAGGTAAG CCAATGGGTT
      TACCGGAAAT GGGTTCATGT AACCCAGTTA CCCTCCATTC GGTTACCCAA 310        320        330        340        350
      TTTCCCATTA CTGGCAAGCA CACTGAGTCA AATGGGACTT CCACTGGGT
      AAAGGGTAAT GACCGTTCGT GTGACTCAGT TTACCCTGAA AGGTGACCCA
```

Fig. 2 (continued)

```
         360        370        380        390        400
    TTTGCCCAAG TACATTGGGT CAATGGGAGG TGAGCCAATG GGAAAAACCC
    AAACGGGTTC ATGTAACCCA GTTACCCTCC ACTCGGTTAC CCTTTTTGGG 410        420        430        440        450
    ATTGCTGCCA AGTACACTGA CTCAATAGGG ACTTTCAATG GGTTTTTCAT
    TAACGACGGT TCATGTGACT GAGTTATCCC TGAAAGTTAC CCAAAAAGTA 460        470        480        490        500
    TGTTGGCAAG CATATAAGGT CAATGTGGGT GAGTCAATAG GGACTTTCCA
    ACAACCGTTC GTATATTCCA GTTACACCCA CTCAGTTATC CCTGAAAGGT 510        520        530        540        550
    TTGTATTCTG CCCAGTACAT AAGGTCAATA GGGGGTGAAT CAACAGGAAA
    AACATAAGAC GGGTCATGTA TTCCAGTTAT CCCCCACTTA GTTGTCCTTT 560        570        580        590        600
    GTCCCATTGG AGCCAAGTAC ACTGCGTCAA TAGGGACTTT CCATTGGGTT
    CAGGGTAACC TCGGTTCATG TGACGCAGTT ATCCCTGAAA GGTAACCCAA 610        620        630        640        650
    TTGCCCAGTA CATAAGGTCA ATAGGGGATG AGTCAATGGG AAAAACCCAT
    AACGGGTCAT GTATTCCAGT TATCCCCTAC TCAGTTACCC TTTTTGGGTA 660        670        680        690        700
    TGGAGCCAAG TACACTGACT CAATAGGGAC TTTCCATTGG GTTTTGCCCA
    ACCTCGGTTC ATGTGACTGA GTTATCCCTG AAAGGTAACC CAAAACGGGT
```

Fig. 2 (continued)

```
          710        720        730        740        750
      GTACATAAGG TCAATAGGGG GTGAGTCAAC AGGAAAGTTC CATTGGAGCC
      CATGTATTCC AGTTATCCCC CACTCAGTTG TCCTTTCAAG GTAACCTCGG 760        770        780        790        800
      AAGTACATTG AGTCAATAGG GACTTTCCAA TGGGTTTTGC CCAGTACATA
      TTCATGTAAC TCAGTTATCC CTGAAAGGTT ACCCAAAACG GGTCATGTAT 810        820        830        840        850
      AGGTCAATGG GAGGTAAGCC AATGGGTTTT TCCCATTACT GGCACGTATA
      TCCAGTTACC CTCCATTCGG TTACCCAAAA AGGGTAATGA CCGTGCATAT 860        870        880        890        900
      CTGAGTCATT AGGGACTTTC CAATGGGTTT TGCCCAGTAC ATAAGGTCAA
      GACTCAGTAA TCCCTGAAAG GTTACCCAAA ACGGGTCATG TATTCCAGTT 910        920        930        940        950
      TAGGGGTGAA TCAACAGGAA AGTCCCATTG GAGCCAAGTA CACTGAGTCA
      ATCCCCACTT AGTTGTCCTT TCAGGGTAAC CTCGGTTCAT GTGACTCAGT 960        970        980        990        1000
      ATAGGGACTT TCCATTGGGT TTTGCCCAGT ACAAAAGGTC AATAGGGGGT
      TATCCCTGAA AGGTAACCCA AAACGGGTCA TGTTTTCCAG TTATCCCCCA 1010       1020       1030       1040       1050
      GAGTCAATGG GTTTTTCCCA TTATTGGCAC GTACATAAGG TCAATAGGGG
      CTCAGTTACC CAAAAAGGGT AATAACCGTG CATGTATTCC AGTTATCCCC
```

Fig. 2 (continued)

```
      1060       1070       1080       1090       1100
TGAGTCATTG GGTTTTTCCA GCCAATTTAA TTAAAACGCC ATGTACTTTC
ACTCAGTAAC CCAAAAAGGT CGGTTAAATT AATTTTGCGG TACATGAAAG 1110       1120       1130       1140       1150
CCACCATTGA CGTCAATGGG CTATTGAAAC TAATGCAACG TGACCTTTAA
GGTGGTAACT GCAGTTACCC GATAACTTTG ATTACGTTGC ACTGGAAATT 1160       1170       1180       1190       1200
ACGGTACTTT CCCATAGCTG ATTAATGGGA AAGTACCGTT CTCGAGCCAA
TGCCATGAAA GGGTATCGAC TAATTACCCT TTCATGGCAA GAGCTCGGTT 1210       1220       1230       1240       1250
TACACGTCAA TGGGAAGTGA AAGGGCAGCC AAAACGTAAC ACCGCCCCGG
ATGTGCAGTT ACCCTTCACT TTCCCGTCGG TTTTGCATTG TGGCGGGGCC 1260       1270       1280       1290       1300
TTTTCCCTGG AAATTCCATA TTGGCACGCA TTCTATTGGC TGAGCTGCGT
AAAAGGGACC TTTAAGGTAT AACCGTGCGT AAGATAACCG ACTCGACGCA 1310       1320       1330       1340       1350
TCACGTGGGT ATAAGAGGCG CGACCAGCGT CGGTACCGTC GCAGTCTTCG
AGTGCACCCA TATTCTCCGC GCTGGTCGCA GCCATGGCAG CGTCAGAAGC 1360       1370       1380
GTCTGACCAC CGTAGAACGC AGAGCTCCTC GCTGCAG
CAGACTGGTG GCATCTTGCG TCTCGAGGAG CGACGTC
```

PROMOTER SYSTEM

This application is a continuation-in part of U.S. Ser. No. 810,819, filed Dec. 18, 1985, the contents of which are hereby incorporated herein by reference.

Advances in genetic engineering, especially over the last decade, have made possible in certain cases the in vitro synthesis of heterologous proteins. Typically a nucleotide sequence encoding the heterologous protein is introduced into cultured host cells via a vector in which the nucleotide sequence is operatively linked to expression control sequences, including a transcriptional promoter and transcriptional and translational start and termination signals. The engineered host cells are then cultured under suitable conditions permitting expression of the heterologous protein under the transcriptional control of the promoter.

Changes in the rate and specificity of transcription are key events in gene expression. Rapid advances in recombinant-DNA technology have facilitated intensive analyses of numerous cellular and viral genes. These studies have revealed that, for genes coding for polypeptide products in eucaryotes, the transcriptional promoter sequences are typically located upstream of the initiation site(s) of RNA transcripts, the cap site(s). A "TATA" box and a "CAAT" box are located approximately 30 nucleotides and 80 nucleotides, respectively, upstream of the cap site(s) (Corden, J. et al., 1980, Science 209:1406–1414 and Breathnach, R. and Chambon, P., 1981, Annual Review of Biochemistry 50:349–383). Transcriptional modulator elements located more than 110 bp upstream of eucaryotic genes have been described more recently. Such upstream sequences essential for the expression of the early genes of the simian and murine DNA tumor viruses, simian virus 40 (SV40) and polyomavirus (Py), respectively, are the archetypes of a class of gene control elements now commonly called "enhancers". Transcriptional enhancers are cis-acting DNA sequences which, when isolated and linked to a variety of genes, dramatically increase transcription without increasing template copy number and which can function over much greater distances than other expression control components, usually in either orientation (Banerji, J. et al., 1981, Cell 27:299–308 and deVilliers, J. and Schaffner, W., 1981, Nucleic Acids Research 9:6251–6264. Enhancers have since been identified in many viral genomes, including the human and murine cytomegaloviruses (hCMV: Boshart, M. et al., 1985, Cell 41:521–530; mCMV: Dorsch-hHasler, K. et al., 1985, Proc. Natl Acad. Sci. 82:8325–8329), as well as in association with cellular genes.

Several eucaryotic promoters, notably those recognized by eucaryotic RNA polymerase II, have been used with varying degrees of success in individual cases for the in vitro expression of heterologous DNA. These include promoters such as the early gene promoters of simian virus 40 and polyoma-virus, retroviral long terminal repeats (LTR's) and cellular gene promoters such as the mouse metallothionein gene promoter.

Cytomegaloviruses (CMV's), members of the herpesviridae, have been isolated from a number of different species and described in the scientific literature. Some strains of CMV's are on deposit with the American Type Culture Collection (Rockville, Md., USA), e.g. ATCC Nos. VR706, VR538, VR807, VR536 and VR194. Two groups have reported the molecular characterization and cloning of the genome of mouse cytomegalovirus (mCMV), also known as mouse salivary gland virus (Smith strain)(see e.g. Ebeling, A. et al., 1983, J. Virol. 47(3):421–433 and Mercer et al., 1983, Virol. 129:94–106).

This invention achieves significantly enhanced in vitro expression levels of heterologous proteins by inserting into host cells DNA encoding the heterologous proteins under the transcriptional control of DNA fragments derived from the mCMV immediate early gene regulatory sequences. These fragments include an approximately 2270 bp restriction endonuclease fragment isolated from the viral genome, truncated versions of this fragment and hybrid promoters, constructed in vitro by combining transcription promoter sequences derived from this fragment with regulatory sequences derived from other transcriptional units. Furthermore, I have surprisingly found that truncation of the 2270 base pair fragment results in significant improvement in the efficacy of the DNA fragment as a promoter in heterologous constructions. In addition, I have found that novel hybrid promoters, constructed in vitro by combining mouse CMV immediate early promoter components with enhancer elements isolated from other transcription units, can be even more effective than natural "wild type" promoter fragments.

More specifically, this invention provides a recombinant DNA molecule which comprises a nucleotide sequence encoding a heterologous protein operatively linked to the approximately 2.27 kilobase pair Pst I restriction fragment of the mCMV genome containing the mouse cytomegalovirus immediate early promoter or to an effective expression promoting fragment thereof. The fragment may comprise the 1387 base pair (bp) Hpa I/Pst I fragment or the 196 bp Xho I/Pst I fragment of the larger Pst I fragment, for example, or may comprise another effective expression promoting fragment which comprises a nucleotide sequence capable of hybridizing to the nucleotide sequence depicted in FIG. 2. That sequence comprises the nucleotide sequence of the HpaI/PstI fragment, also referred to herein as the "1400 bp" fragment or segment, and contains the mCMV immediate early promoter.

This invention further provides a hybrid transcription unit comprising an above-mentioned recombinant DNA molecule functionally linked to a heterologous transcriptional regulatory sequence, e.g. a heterologous enhancer such as the SV40 or polyomavirus transcriptional enhancer, as described in greater detail below. For the purposes of this disclosure, the term "heterologous" as applied to a protein or DNA sequence means a protein or DNA sequence not present in the genome of naturally-occurring mCMV.

This invention further encompasses a eucaryotic host cell which contains an above-mentioned recombinant DNA molecule or hybrid transcriptional unit, and a method for producing a heterologous protein, which method involves culturing such a host cell under suitable conditions permitting cell growth and gene expression.

The use of novel DNA fragments bearing the mCMV immediate early promoter, or derivatives thereof, to drive the expression of heterologous proteins can utilize parameters which are conventional in in vitro cell culture systems.

In particular I employ an approximately 2,270 base pair (bp) DNA restriction fragment of the mCMV genome and truncated and hybrid derivatives thereof. The 2270 bp fragment can be obtained by PstI digestion of mCMV (Smith Strain ATCC No. VR194) DNA, followed by preparative agarose gel electrophoretic separation of the digestion products using conventional techniques. The shorter 1387 bp derivative thereof is prepared and inserted into expression vectors by HpaI cleavage at a unique site within the PstI fragment, followed by ligation of the blunt DNA end so generated to a blunt end of vector DNA, as illustrated in greater detail in Example 2, below. A shorter 196 bp derivative thereof is prepared and inserted into expression vectors by XhoI cleavage at a unique site within either of the larger fragments followed by ligation of the DNA end so generated to vector DNA, as illustrated in greater detail in Example 2, below. Hybrid derivatives of the mCMV promoter are prepared by insertion of transcriptional regulatory DNA fragments, isolated from SV40, polyomavirus or other transcriptional units, in place of deleted mCMV DNA sequences, also as illustrated in greater detail in Example 2, below.

The ability of such promoter fragments to drive expression of the bacterial chloramphenicol acetyl transferase (CAT) gene was quantitated as described in Example 3, and the expression levels so obtained compared to those obtained with other strong eucaryotic promoters. The 2270 bp mCMV DNA fragment was found to bear a very strong promoter, as evidenced by superior levels of CAT gene product enzymatic activity in lysates of transfected mammalian cells. Surprisingly, the truncated 1387 bp fragment was found to be even more efficient than the longer fragment in promoting heterologous gene expression in certain cell lines. This unexpected increase in promoter activity probably indicates the existence of one or more elements in the 2270 bp fragment which in at least some cells negatively influence transcription of the heterologous gene, here the CAT gene, and which are effectively deleted in the 1387 bp segment. Also surprising is the finding that even the shortest truncated derivative of the mCMV promoter, the 196 bp fragment, retains residual transcriptional promoter activity, which in some cell lines such as chinese hamster ovary (CHO) cells is even more effective than the polyomavirus early promoter. This indicates that sequences within approximately 150 bp of the transcriptional start site, contained within this fragment, can significantly contribute to the overall efficiency of larger mCMV promoter fragments Any fragments, including the nucleotide sequence of the 1387 bp fragment, but nonetheless lacking part or all of the negative element(s) present within the 2270 bp fragment, could also be useful as effective expression control elements in appropriate circumstances. Such intermediate length fragments may be readily obtained by Bal 31 exonuclease digestion of, or otherwise truncating, the 2270 bp fragment by conventional techniques. These intermediate length fragments would be capable of hybridizing to the nucleotide sequence depicted in FIG. 2. The promoter activity of such intermediate length fragments may be readily quantitated and compared with that of the 196 bp fragment, the 1387 bp fragment, 2270 bp fragment and other promoters by conventional methods, including the method set forth in Example 3, below. While the 1387 bp fragment is presently preferred for use in accordance with this invention, longer or shorter sub-fragments of the 2270 bp segment may be useful in individual cases.

A hybrid SV40 enhancer-mCMV fragment was unexpectedly found to be an exceptionally strong promoter of transcription, particularly in human HeLa and chinese hamster CHO cell lines. Similarly, a hybrid polyomavirus enhancer-mCMV fragment was unexpectedly found to be an exceptionally strong transcriptional promoter, particularly in mouse NIH3T3 and CHO cell lines.

These novel hybrid transcriptional promoter sequences clearly demonstrate the potential to combine heterologous transcription regulatory components and thereby construct gene expression vectors with superior utility to naturally occurring counterparts.

The ability of the 2270 bp, the 1387 bp, and 196 bp mCMV DNA promoter fragments, as well as the SV40 enhancer-mCMV promoter (SV-CMV) and polyomavirus enhancer-mCMV promoter (Py-CMV) hybrid fragments to drive the expression of other heterologous eucaryotic genes has been tested. Other heterologous genes as well as the CAT gene were found to be efficiently expressed in a wide variety of cell types, including human, rat, mouse, chinese hamster, monkey and mink cells, of both epithelial and mesenchymal origin.

Recombinant DNA molecules of this invention, e.g. cloning or expression vectors or other viral- or plasmid-derived molecules, thus encompass molecules containing a nucleotide sequence encoding a heterologous protein operatively linked to, i.e. under the expression control of, an effective expression promoting fragment of the mCMV immediate early promoter. The mCMV-derived promoter may thus be the approximately 2270 bp PstI fragment described above or any effective expression promoting fragment thereof such as the 1387 bp HpaI/PstI fragment thereof, the sequence of which is depicted in FIG. 2 or a fragment capable of hybridizing thereto. The mCMV-derived promoter may also thus be a hybrid composed of transcriptional regulatory sequences isolated from other transcription units functionally linked to the mCMV promoter, or truncated derivatives thereof, such as the SV-CMV or Py-CMV promoter fragments described in Example 2 and as depicted in FIG. 1. Host cells transformed with such recombinant DNA molecules may be cultured by conventional techniques as a method for producing the heterologous protein, which may then be recovered and purified.

The use of the mCMV promoter in accordance with this invention is not limited by the heterologous protein desired and is therefore of broad utility in this respect. These promoters also have a very broad host range and functioned with superior efficiency in a wide variety of cell lines tested. These promoters should be useful in a wide variety of vectors, including for example, amplifiable vectors as are known in the art and vectors designed for the identification and isolation of DNA encoding a protein via expression of said protein in mammalian cells (as described for example by Wong G. et al., 1985, Science 228:810-815). Any nucleotide sequence encoding a heterologous protein can easily be inserted into any cloning or expression vector operatively linked to the mCMV promoter, or derivatives thereof, obtained as described. Vector construction may be effected using well known techniques and the vector DNA used to transform the desired host cells. These transformed cells may then be cultured using conventional methodologies and the protein or RNA product(s) isolated and purified as is known in the art.

EXAMPLE I

Derivation and characterization of mCMV immediate early promoter DNA fragments mCMV (mouse salivary gland virus, Smith strain) can be obtained from the American Type Culture Collection, Rockville, MD (ATCC No. VR-194). Virus is propagated in Balb/c mouse embryo fibroblasts and viral DNA prepared as previously described (Eberling et al., 1983, J. Virol. 43(3):421–433).

The approximately 2,270 bp DNA fragment bearing the immediate early promoter can be excised from the mCMV genome by digestion of viral DNA with the restriction endonuclease PstI and the fragment so obtained may be isolated by agarose gel electrophoresis using standard procedures (see Maniatis et al., "Molecular Cloning, A Laboratory Manual", Cold Spring Harbor Laboratory, Cold Spring Harbor, N.Y., 1982). DNA extracted from the appropriate region of the agarose gel may be subcloned into any suitable cloning vector and the presence of the correct PstI fragment insert verified by standard recombinant DNA methodologies, e.g. by hybridization to a labelled DNA probe corresponding to part or all of the sequence presented in FIG. 2, or by restriction analysis.

The 1387 bp truncated derivative of the 2270 bp fragment described above is prepared by an additional cleavage of the larger (i.e. 2270 bp) DNA fragment with the restriction endonuclease HpaI. This site is unique in the larger fragment and generates DNA with blunt ends which therefore can be ligated to any other blunt-ended DNA terminus by using T4 DNA ligase (Maniatis, ibid).

The 196 bp truncated derivative of the larger mCMV immediate early gene promoter fragments (either the 2270 bp or the 1387 bp fragment) is prepared by cleavage at a unique XhoI restriction endonuclease site located between nucleotides numbered 1190 and 1197 in FIG. 2. The DNA ends so generated can be ligated to any compatible DNA terminus by using DNA ligase (Maniatis, Ibid.). The DNA fragments bearing the immediate early promoter described above can be characterized by digestion with numerous restriction endonucleases, including AccI, NdeI, AatII and XhoI, which recognize sites within the DNA sequence depicted in FIG. 2. The DNA sequence of the 1387 bp truncated promoter fragment shown in FIG. 2 has been determined by the dideoxynucleotide chain termination technique (Sanger et al., 1977, Proc Natl. Acad. Sci., USA 74:5463–5467).

EXAMPLE 2

Construction of vectors and CAT expression test DNA's

All plasmid DNA constructs were prepared according to the NIH guidelines governing the use of recombinant DNA and using standard techniques, e.g. as described in Maniatis, et al., (1982). I constructed a number of different eucaryotic expression vector-derivatives, which bear one of the described mCMV immediate early promoter-derived DNA fragments. The subcloning of these fragments into virtually any suitable cloning or expression vector may be effected by routine techniques. The larger (2270 bp) fragment is generated from mCMV viral DNA as a PstI cleavage product, which only has to be orientated such that the heterologous gene to be expressed, or cloning site, is "down stream" of the promoter. Orientation of the DNA fragment is facilitated by the presence of the asymetric XhoI restriction endonuclease recognition site 197 bp from the "downstream" end of the fragment. Since the shorter (1387 bp) fragment is generated by HpaI cleavage of the larger (2270 bp) PstI fragment, orientation of this fragment is easily accomplished because the "upstream" terminus of the fragment is blunt. Similarly, the shorter 196 bp fragment is generated by XhoI cleavage of either of the larger fragments and the orientation of this fragment is easily accomplished because the "upstream" and "down stream" termini can normally only be ligated to unique, compatible DNA ends which are not the same.

In order to quantitate and compare the strengths of these promoter fragments to other promoter sequences, test plasmid DNA's depicted in FIG. 1, were constructed using standard techniques.

These plasmids are derivatives of pPyCAT (Veldman et al., 1985, Mol. Cell. Biol. 5:649–658), which is itself derived from pSV2CAT (Gorman et al., 1982, Mol. Cell. Biol. 2:1044–1051). The CAT plasmid derivatives I constructed have the early promoter of polyomavirus (A2 strain) in pPyCAT replaced by the described mCMV promoter-derived fragments, as depicted in FIG. 1. Each mCMV promoter-derived fragment is orientated such that the bacterial chloramphenicol acetyl transferase (CAT) gene is adjacent to the transcriptional capsite(s), and "downstream" of the transcriptional promoter. This was accomplished by first removing a Hind III to EcoRI DNA fragment bearing the polyomavirus early promoter from the pPyCAT plasmid and replacing it with the 2270 bp mCMV DNA fragment, using synthetic oligonucleotide adapter fragments and employing conventional methods. The other CAT plasmid derivatives described below were then derived from this construct, named pmCMVCAT. These are: pmCMV1387CAT; pmCMV196CAT; pSVmCMVCAT; pPymCMVCAT (see FIG. 1). The DNA plasmids so constructed were used to transform competent E. coli HB101 cells to ampicillin resistance. This allowed cloning, identification, isolation and molecular characterization of the desired plasmids using standard techniques described by Maniatis et al. (1982).

EXAMPLE 3

Figure 1A:
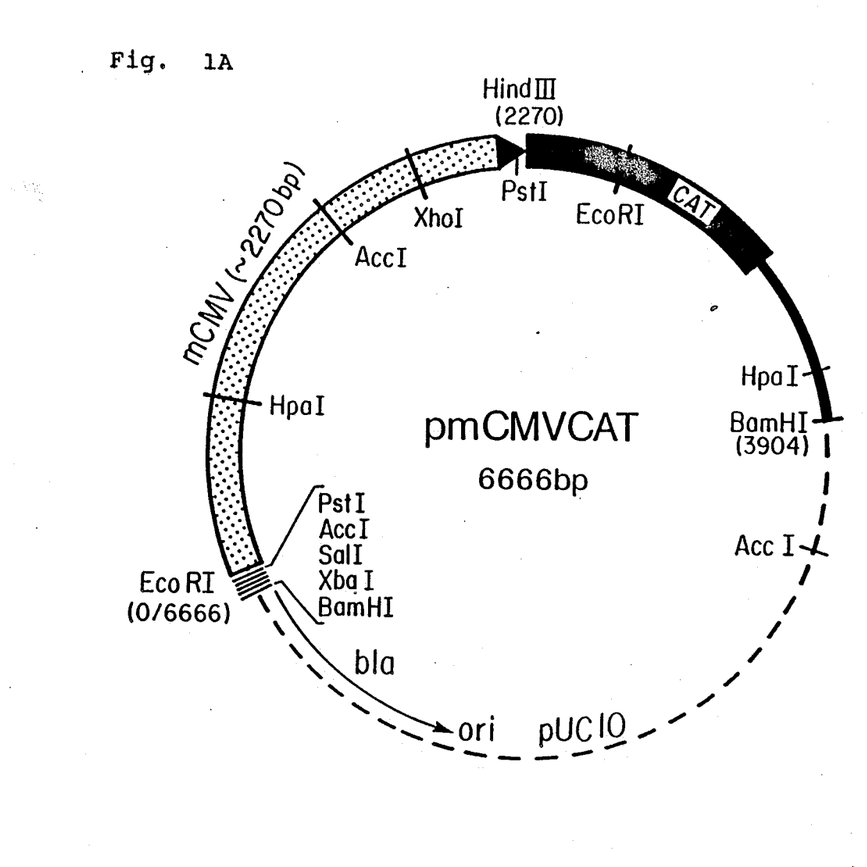
Figure 1B:
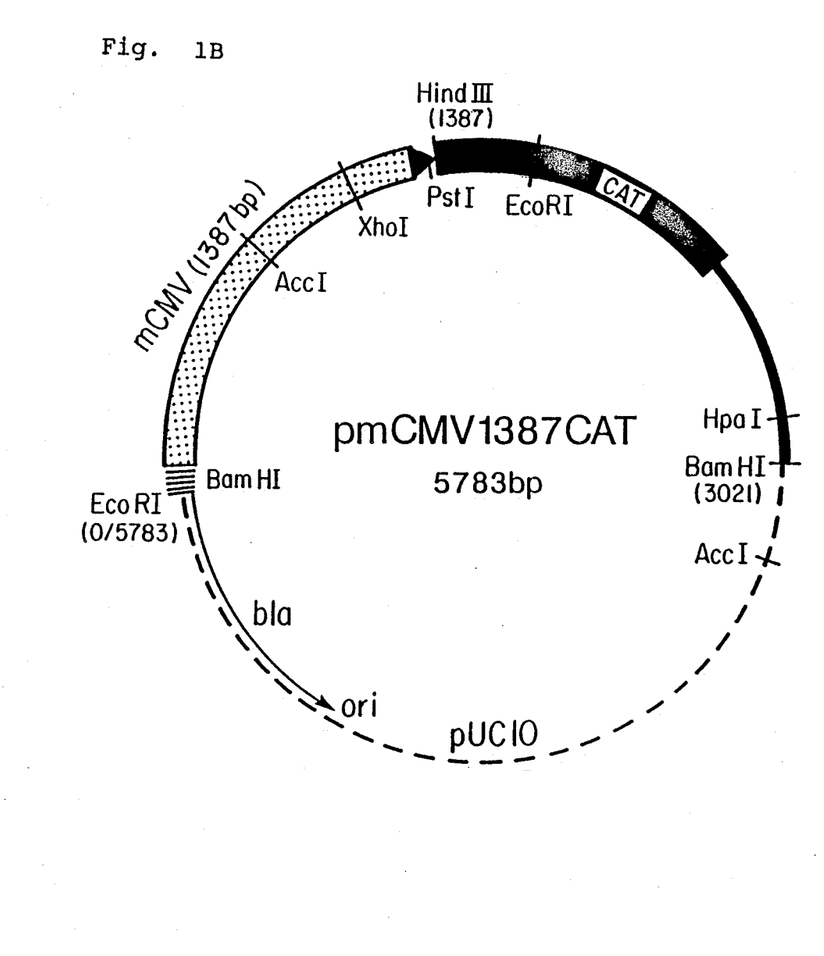
Figure 1C:
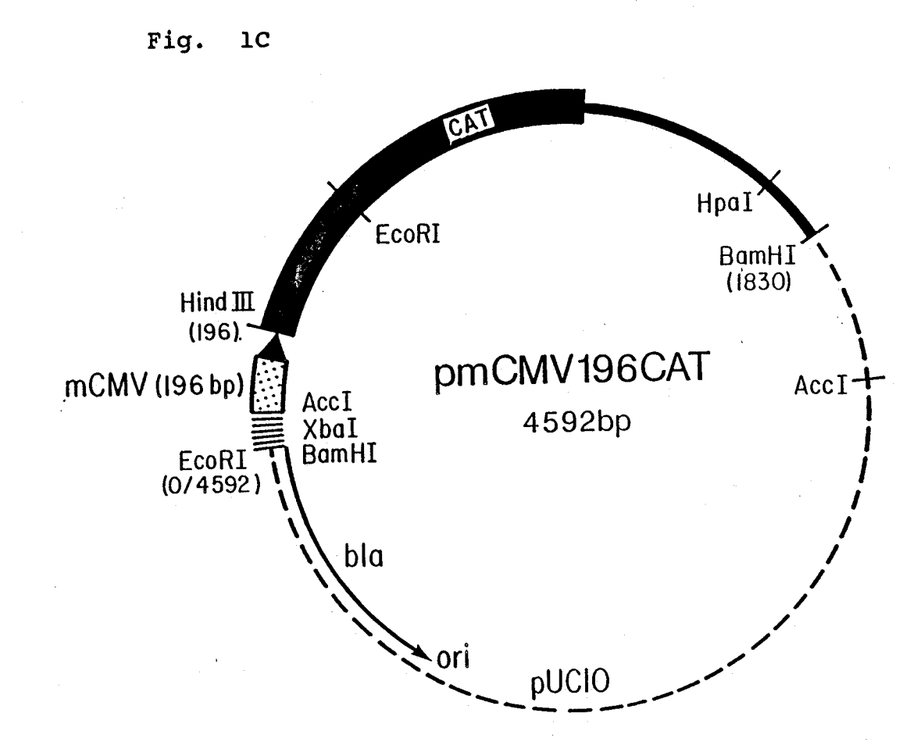
Figure 1D:
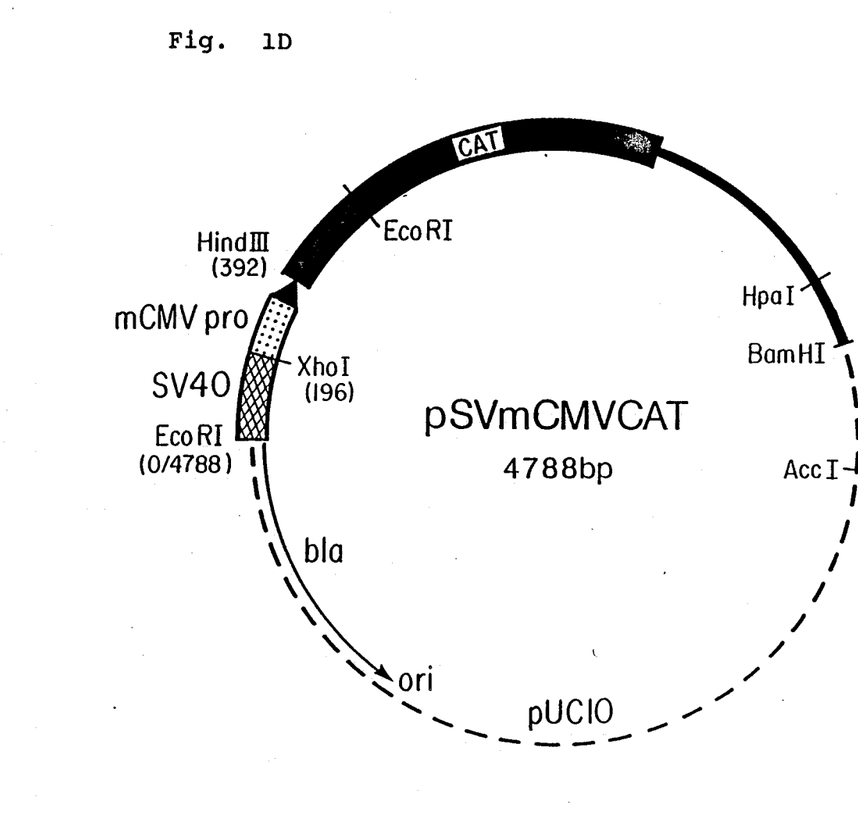
Figure 1E:
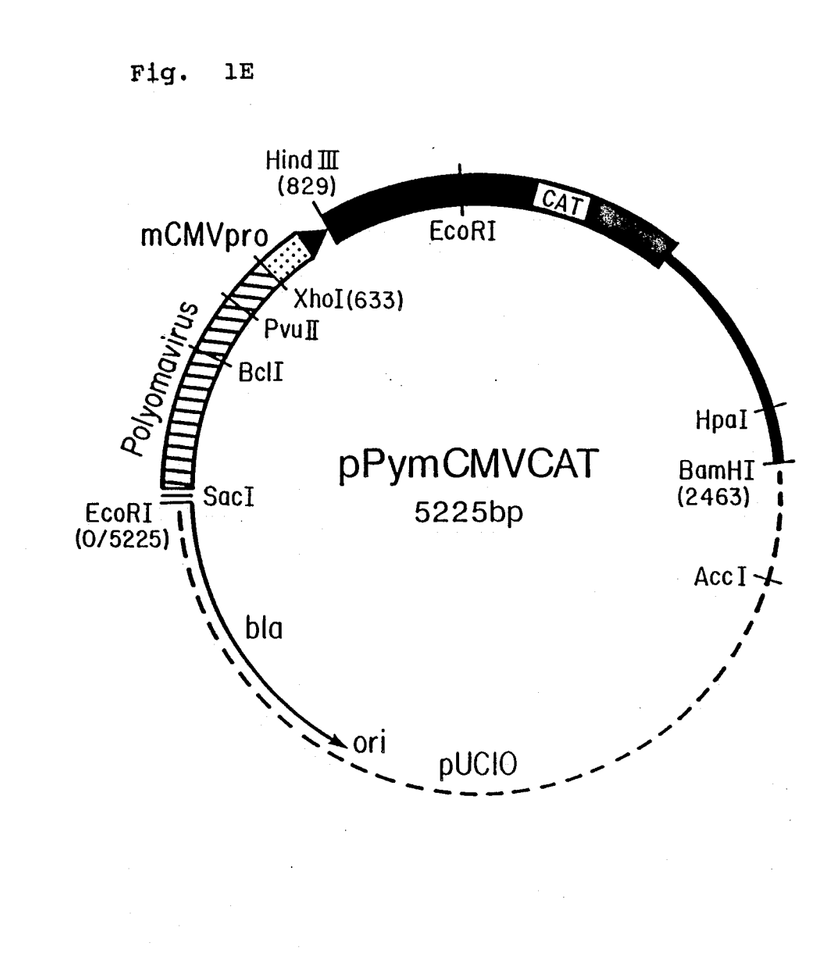
Figure 2:
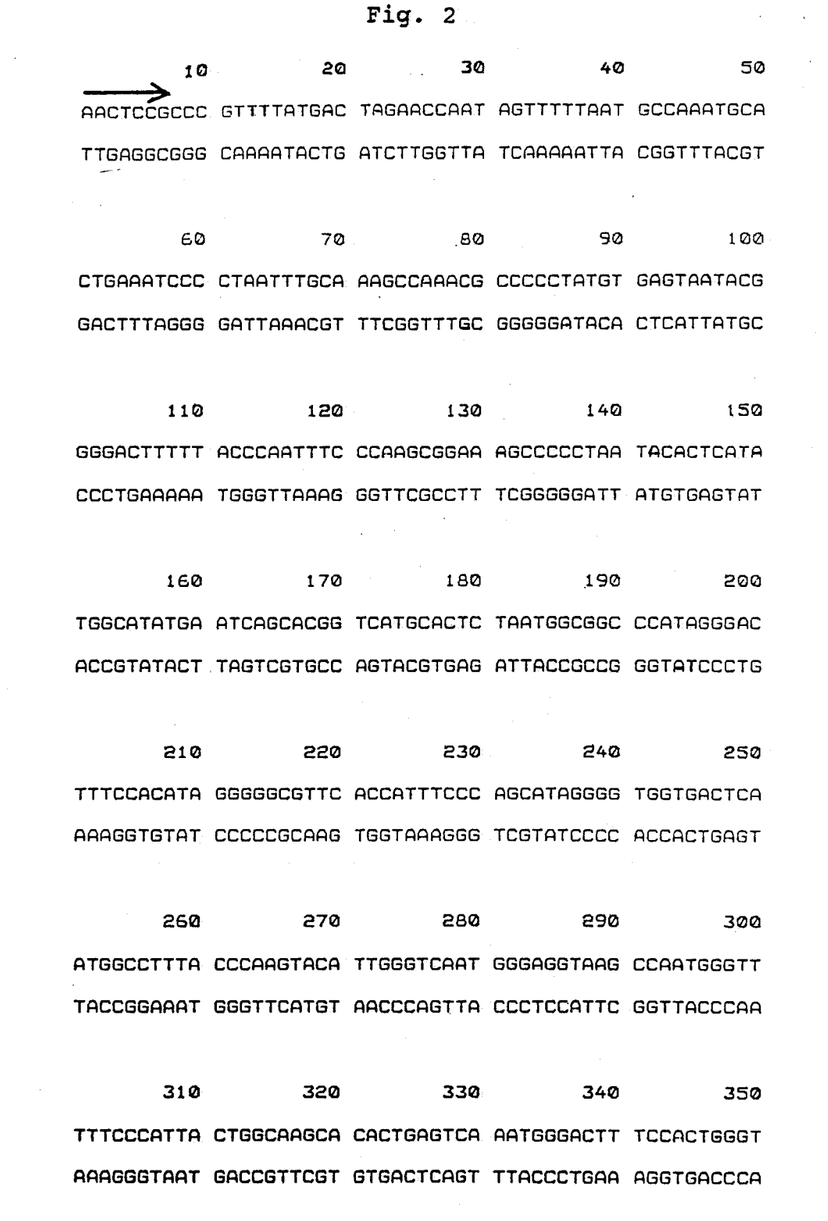

Quantitative Analyses of Heterologous Gene Expression in Cultured Mammalian Cells To quantitate the expression of the bacterial chloramphenicol acetyl transferase (CAT) gene in mammalian cells, driven by the SV40 early promoter or polyomavirus early promoter, the described 2270 bp mCMV immediate early promoter fragment, the truncated 1387 bp and 196 bp derivatives thereof and the SV40-mCMV and polyomavirus-mCMV hybrid derivatives thereof, DNA of each of the following plasmids was purified:

pSV2CAT (Gorman et al., 1982, Mol. Cell. Biol., 2:1044–1051), which has the SV40 early promoter driving expression of the CAT gene; ATCC No. 37155)

pPyCAT (Veldman et al., 1985, Mol. Cell. Biol., 5:649–658), which has CAT expression driven by the polyomavirus early promoter pmCMVCAT, a derivative of the above pPyCAT which has the larger (2270 bp) mCMV PstI promoter fragment replacing the polyomavirus early promoter (see FIG. 1A)

pmCMV1387CAT, analogous plasmid with the truncated 1387 bp mCMV HpaI/PstI fragment replacing the polyomavirus promoter (see FIG. 1B).

pmCMV196CAT, an analogous plasmid with the truncated 196 bp mCMV XhoI/PstI fragment replacing the polyomavirus promoter (see FIG. 1C).

pSVmCMVCAT, a plasmid construct derived from pmCMV196CAT, with a hybrid promoter comprising the 196 bp XhoI/PstI promoter fragment of mCMV functionally linked to a 196 bp SV40 XhoI transcriptional enhancer-bearing fragment (nucleotides 100–296, deVilliers J. et al., 1982, Nucleic Acids Research 10:7965–7976) (FIG. 1D).

pPymCMVCAT, an analogous plasmid, with a hybrid promoter comprising the 196 bp XhoI/PstI promoter fragment of mCMV functionally linked to an approximately 633 bp polyomavirus BamHI/XhoI transcriptional enhancer-bearing fragment from Polyoma strain A2 (ATCC 45017) (nucleotides 4632–5265, Tyndall, C. et al., 1981, Nucleic Acids Research 9:6231–6250; FIG. 1E).

Plasmid DNA's were isolated from bacterial cultures using conventional techniques and purified by two successive CsCl density gradient centrifugation steps. These purified DNA's were then separately introduced into a variety of cultured mammalian cells including human, rat, mouse, Chinese hamster, monkey and mink cells of both epithelial and mesenchymal origin. This was done either by the calcium phosphate coprecipitation technique or the DEAE-dextran technique (as described previously by deVilliers and Schaffner in Techniques in Nucleic Acid Biochemistry, Volume B5, ed. R.A. Flavell, Elsevier Scientific Publishers, Ireland (1983)). The transfected mammalian cells were lysed 48 hours post-transfection and the activity of chloramphenicol acetyl transferase in the lysates assayed as originally described (Gorman et al., 1982, Mol. Cell. Biol. 2:1044–1051). The ability of such promoter fragments to drive expression of the bacterial chloramphenicol acetyl transferase gene was quantitated by densitometer tracing of autoradiograms obtained by standard techniques. The 2270 bp mCMV DNA fragment was found to bear a very strong promoter. Surprisingly, the 1387 bp truncated fragment thereof was found to be even more efficient in certain cell lines and even the shortest, truncated derivative, the 196 bp fragment retained considerable residual transcription promoter activity. Of great significance was the finding that the SV40 enhancer mCMV promoter hybrid and the polyomavirus enhancer-mCMV promoter hybrid were even more efficient than the "wild-type" promoter fragments in certain lines. It was also revealed that the above mentioned transcriptional promoters have a broad range of utility as the CAT gene was found to be efficiently expressed in a wide variety of cell types derived from different species and also lineages.

What is claimed is:

1. A hybrid transcription unit comprising a recombinant DNA molecule or which comprises a nucleotide sequence encoding a heterologous protein operatively linked to the approximately 2.27 kilobase pair PstI restriction fragment of the mCMV genome containing the mouse cytomegalovirus (mCMV) immediate early promoter or to an effective expression promoting fragment thereof functionally linked to a heterologous transcriptional enhancer.

2. A hybrid transcription unit of claim 1 wherein the heterologous enhancer comprises the SV40 or polyomavirus transcriptional enhancer.

3. A eucaryotic host cell containing the hybrid transcription unit of claim 1.

4. A eucaryotic host cell containing the hybrid transcription unit of claim 2.

5. A method for producing a heterologous protein which comprises culturing host cells of claim 4 under suitable conditions permitting cell growth and gene expression.

* * * * *